(12) United States Patent
Biggadike et al.

(10) Patent No.: US 7,531,528 B2
(45) Date of Patent: *May 12, 2009

(54) FORMULATION CONTAINING ANTI-INFLAMMATORY ANDROSTANE DERIVATIVES

(75) Inventors: Keith Biggadike, Stevenage (GB); Amyn Sayani, Mississauga, CA (US); Ian Buxton, Mississauga, CA (US); Kenton Reed, Mississauga, CA (US)

(73) Assignee: Glaxo Group Limited, Greenford, Middlesex (GB)

( * ) Notice: Subject to any disclaimer, the term of this patent is extended or adjusted under 35 U.S.C. 154(b) by 760 days.

This patent is subject to a terminal disclaimer.

(21) Appl. No.: 10/918,770

(22) Filed: Aug. 13, 2004

(65) Prior Publication Data

US 2005/0026888 A1    Feb. 3, 2005

Related U.S. Application Data

(63) Continuation of application No. 10/066,951, filed on Feb. 4, 2002, now Pat. No. 6,787,532, which is a continuation-in-part of application No. 09/958,050, filed as application No. pct/gb01/03495 on Aug. 3, 2001, now Pat. No. 7,101,866.

(30) Foreign Application Priority Data

Aug. 5, 2000    (GB)    ................................ 0019172.6

(51) Int. Cl.
A61K 31/58    (2006.01)
(52) U.S. Cl. ...................................... 514/172
(58) Field of Classification Search ................... 514/172
See application file for complete search history.

(56) References Cited

U.S. PATENT DOCUMENTS

| | | | |
|---|---|---|---|
| 2,837,464 A | 6/1958 | Nobile | |
| 3,067,197 A | 12/1962 | Agnello et al. | |
| 3,312,590 A | 4/1967 | Elks et al. | |
| 3,506,694 A | 4/1970 | Oxley | |
| 3,557,162 A | 1/1971 | Voorschoten et al. | |
| 3,639,434 A | 2/1972 | Oxley et al. | |
| 3,755,302 A | 8/1973 | Ercoli et al. | |
| 3,828,080 A | 8/1974 | May et al. | |
| 3,856,828 A | 12/1974 | Phillips et al. | |
| 3,891,631 A | 6/1975 | Phillips et al. | |
| 3,981,894 A | 9/1976 | Phillips et al. | |
| 3,989,686 A | 11/1976 | Phillips et al. | |
| 4,093,721 A | 6/1978 | Phillips et al. | |
| 4,113,680 A | 9/1978 | Kamano et al. | |
| 4,187,301 A | 2/1980 | Edwards | |
| 4,188,385 A | 2/1980 | Edwards | |
| 4,198,403 A | 4/1980 | Alvarez | |
| 4,221,787 A | 9/1980 | Bodor et al. | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillips et al. | |
| 4,377,575 A | 3/1983 | Phillips et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Jouveinal | |
| 4,992,474 A | 2/1991 | Skidmore et al. | |
| 4,994,439 A | 2/1991 | Longnecker et al. | |
| 4,996,335 A | 2/1991 | Bodor | |
| 5,063,222 A | 11/1991 | Komoto et al. | |
| 5,081,113 A | 1/1992 | Claussner et al. | |
| 5,202,316 A | 4/1993 | Claussner et al. | |
| 5,250,293 A | 10/1993 | Gleich | |
| 5,362,721 A | 11/1994 | Stache et al. | |
| 5,420,120 A | 5/1995 | Boltralik | |
| 5,608,093 A | 3/1997 | Stache et al. | |
| 5,658,549 A | 8/1997 | Akehurst et al. | |
| 5,707,984 A | 1/1998 | Tjoeng et al. | |
| 5,837,699 A | 11/1998 | Sequeira et al. | |
| 5,849,265 A | 12/1998 | Li-Bovet et al. | |
| 5,889,015 A | 3/1999 | Sequeira et al. | |
| 5,919,776 A | 7/1999 | Hagmann et al. | |
| 5,972,920 A | 10/1999 | Seidel | |
| 5,981,517 A | 11/1999 | Bodor | |
| 6,057,307 A | 5/2000 | Sequeira et al. | |
| 6,127,353 A | 10/2000 | Yuen et al. | |
| 6,136,294 A | 10/2000 | Adjei et al. | |
| 6,197,761 B1 | 3/2001 | Biggadike et al. | |
| 6,261,539 B1 | 7/2001 | Adjei et al. | |
| 6,395,300 B1 | 5/2002 | Straub et al. | |
| 6,537,983 B1 | 3/2003 | Biggadike et al. | |
| 6,921,757 B2 | 7/2005 | Cuenoud et al. | |
| 7,244,742 B2 | 7/2007 | Pieper et al. | |

(Continued)

FOREIGN PATENT DOCUMENTS

BE    889563    11/1981

(Continued)

OTHER PUBLICATIONS

Janette M. Mahoney et al., "Drug effects on the neovascularization response to silver nitrate cauterization of the rat cornea" Current Eye Research, vol. 4, No. 5, 1985, pp. 531-535.

(Continued)

*Primary Examiner*—Barbara P Badio
(74) *Attorney, Agent, or Firm*—James P. Riek

(57) ABSTRACT

There is provided according to the invention a pharmaceutical formulation comprising an aqueous carrier liquid having dissolved therein (a) an ester of fluticasone or a solvate thereof as medicament and (b) a solubilizing agent for assisting the solubilization of the medicament in the aqueous carrier liquid.

14 Claims, No Drawings

U.S. PATENT DOCUMENTS

| | | | |
|---|---|---|---|
| 2002/0081266 A1 | 6/2002 | Woolfe et al. |
| 2002/0103392 A1 | 8/2002 | Stache et al. |
| 2002/0165211 A1 | 11/2002 | Biggadike et al. |
| 2002/0173496 A1 | 11/2002 | Biggadike |
| 2002/0177581 A1 | 11/2002 | Biggadike |
| 2003/0018019 A1 | 1/2003 | Meade et al. |
| 2003/0073676 A1 | 4/2003 | Biggadike et al. |
| 2003/0109511 A1 | 6/2003 | Biggadike et al. |
| 2003/0144257 A1 | 7/2003 | Biggadike et al. |
| 2003/0158163 A1 | 8/2003 | Cuenoud et al. |
| 2004/0053904 A1 | 3/2004 | Komoto et al. |
| 2005/0163724 A1 | 7/2005 | Miyadai et al. |

FOREIGN PATENT DOCUMENTS

| | | |
|---|---|---|
| DE | 1059906 | 6/1959 |
| DE | 2336693 | 2/1975 |
| DE | 2538569 | 3/1977 |
| EP | 0004773 | 10/1979 |
| EP | 0057401 | 8/1982 |
| EP | 0135476 | 3/1985 |
| EP | 0179583 | 4/1986 |
| EP | 0393658 | 10/1990 |
| EP | 0416951 | 3/1991 |
| EP | 0418716 | 3/1991 |
| EP | 0521455 | 1/1993 |
| EP | 0640616 | 3/1995 |
| EP | 0646593 | 4/1995 |
| FR | 580494 | 10/1986 |
| GB | 1191965 | 5/1970 |
| GB | 1384372 | 2/1975 |
| GB | 1438940 | 6/1976 |
| GB | 1517278 | 7/1978 |
| GB | 2079755 | 1/1982 |
| GB | 2088877 B | 6/1982 |
| GB | 2140800 | 12/1984 |
| GB | 1296458 | 8/2008 |
| IL | 109656 | 2/1998 |
| JP | 04208267 | 7/1992 |
| JP | 8291072 | 11/1996 |
| JP | 8291073 | 11/1996 |
| WO | 8903390 | 4/1989 |
| WO | 9015816 | 12/1990 |
| WO | 9104252 | 4/1991 |
| WO | 92/14472 | 9/1992 |
| WO | 94/21229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | 9721721 | 6/1997 |
| WO | 9721724 | 6/1997 |
| WO | 97/24365 | 7/1997 |
| WO | 9740836 | 11/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | 99/32089 | 7/1999 |
| WO | 00/16814 | 3/2000 |
| WO | 00/33892 | 6/2000 |
| WO | 00/38811 | 7/2000 |
| WO | 00/57401 | 8/2000 |
| WO | 0049993 | 8/2000 |
| WO | 0066522 | 11/2000 |
| WO | 01/04118 | 1/2001 |
| WO | 01/15744 | 3/2001 |
| WO | 01/20331 | 3/2001 |
| WO | 0120331 | 3/2001 |
| WO | 01/54664 | 8/2001 |
| WO | 01/62722 | 8/2001 |
| WO | 0154481 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/00199 | 1/2002 |
| WO | 02/00679 | 1/2002 |
| WO | 02/07767 | 1/2002 |
| WO | 02/08243 | 1/2002 |
| WO | 0202565 | 1/2002 |
| WO | 02/12265 | 2/2002 |
| WO | 02/12266 | 2/2002 |
| WO | 02/13868 | 2/2002 |
| WO | 02/26723 | 4/2002 |
| WO | 02036106 | 5/2002 |
| WO | 02/053186 | 7/2002 |
| WO | 02051422 | 7/2002 |
| WO | 02/066422 | 8/2002 |
| WO | 02/070490 | 9/2002 |
| WO | 02/076933 | 10/2002 |
| WO | 02/085296 | 10/2002 |
| WO | 02/088167 | 11/2002 |
| WO | 02/100879 | 12/2002 |
| WO | 03000241 | 1/2003 |
| WO | 03/013427 | 2/2003 |
| WO | 03/033000 | 4/2003 |
| WO | 03/035668 | 5/2003 |
| WO | 03/040691 | 5/2003 |
| WO | 03/042229 | 5/2003 |
| WO | 03/042230 | 5/2003 |
| WO | 03048181 | 6/2003 |
| WO | 03062259 | 7/2003 |
| WO | 03064445 | 8/2003 |
| WO | 03066656 | 8/2003 |
| WO | 03072592 | 9/2003 |
| WO | 03086399 | 10/2003 |
| WO | 03105859 A1 | 12/2003 |
| WO | 2004013156 | 2/2004 |
| ZA | 872389 | 4/1987 |

OTHER PUBLICATIONS

Richard A. Kenley et al., "An Automated, Column-Switching HPLC Method for Analyzing Active and Excipient Materials in Both Cream and Ointment Formulations," Drug Development and Industrial Pharmacy, vol. 11 (9&10), 1985, pp. 1781-1796.

R. Woodford et al., "Activity and bioavailability of a new steroid (Timobesone acetate) in cream and ointment compared with Lidex and Dermovate creams and ointments and Betnovate cream" Int'l Journal of Pharmaceutics, vol. 26 (1985) pp. 145-155.

Denis J. Kertesz et al., "Thiol Esters from Steroid 17β-Carboxylic Acids: Carboxylate Activation and Internal Participation by 17 α-Acylates" J. Org. Chem., vol. 51, 1986, pp. 2315-2328.

Popper, T.L., et al., "Structure-Activity Relationship of a series of novel topical corticosteroids", Journal of Steroid Biochemistry 1987, vol. 27, 840-841.

Shapiro, E.L., et al. Al., "17 Heteroaroyl Esters of Corticosteroids 2. 11 Beta Hydroxy Series." Journal of Medicinal Chemistry, American Chemical Society, Washington, US, vol. 30, No. 9, 1987, pp. 1581-1588.

John T. H. Ong et al., "Micellar Solubilization of Timobesone Acetate in Aqueous and Aqueous Propylene Glycol Solutions of Nonionic Surfactants", Pharmaceutical Research, vol. 5, No. 11, 1988, pp. 704-708.

John T. H. Ong et al., Intrinsic Potencies of Novel Thiol Ester Corticosteroids RS-85095 and RS-21314 as Compared With Clobetasol 17-Propionate and Fluocinonide Arch Dermatol, vol. 125, Dec. 1989, pp. 1662-1665.

Isogai, Mitsutaka, et al., "Binding affinities of Mometasone Furoate and related compounds including its Metabolites for the Glucocorticoid Receptor of Rat Skin Tissue" J. Steroid Biochem. Mol. Biol. 1993, vol. 44, 141-145.

Phillips, GH et al., "Synthesis and structure activity Relationships in a series of Anti-inflammatory Corticosteroid Analogues, Halomethyl Androstane—17B-carbothioates and—17B-carboselenoates," Journal of Medicinal Chemistry 1994, 37, 3717-3729.

S.J. Lane et al., "Evaluation of a New Capillary Electrochromatography/Mass Spectrometry Interface Using Short Columns and High Field Strengths for Rapid and Efficient Analyses," Rapid Communications in Mass Spectrometry, vol. 10, 1996, pp. 733-736.

Franklin I. Aigbirhio et al., "Automated Radiosynthesis of No-carrier-added [$S$-$fluoromethyl$-$^{18}F$]Fluticasone Propionate as a Radiotracer for Lung Deposition Studies with PET" Journal of Labelled Compounds and Radiopharmaceuticals, vol. 39, No. 7, 1997, pp. 569-584.

Nisha Mistry et al., "Characterisation of impurities in bulk drug batches of fluticasone propionate using directly coupled HPLC-NMR spectroscopy and HPLC-MS," Journal of Pharmaceutical and Biomedical Analysis vol. 16, 1997, pp. 697-705.

Knobil, K., et al. Al., "Adding Salmeterol Is More Effective Than Increasing The Dose Of Fluticasone For Patients With Asthma Who Are Symptomatic On Low Dose Fluticasone," European Respiratory review, Copenhagen, DK, vol. 12, No. SUPPL 29 Dec. 1998, pp. 19S-20S.

Nisha Mistry et al., Impurity profiling in bulk pharmaceutical batches using 19F NMR spectroscopy and distinction between monomeric and dimeric impurities by NMR-based diffusion measurements, Journal of Pharmaceutical and Biomedical Analysis, vol. 19, 1999, pp. 511-517.

N. Smith et al., "Comparison of the electroosmotic flow profiles and selectivity of stationary phases used in capillary electrochromatography," Journal of Chromatography A., vol. 832, 1999, pp. 44-54.

R.C. Garner et al., "A validation study comparing accelerator MS and liquid scintillation counting for analysis of $^{14}$C-labelled drugs in plasma, urine and faecal extracts", Journal of Pharmaceutical and Biomedical Analysis vol. 24, 2000, pp. 197-209.

Harold S. Nelson et al. "Fluticasone propionate/salmeterol combination provides more effective asthma control than low-dose inhaled corticosteroid plus montelukast," J. Allergy Clin. Immunol., vol. 106, No. 6, Dec. 2000, pp. 1088-1095.

Gunnar Johansson et al., "Comparison of Salmeterol/Fluticasone Propionate Combination With Budesonide in Patients With Mild-to-Moderate Asthma" Clin. Drug Invest. vol. 21, No. 9, 2001, pp. 633-642.

Bertil Pettersson et al., Re-evaluation of the classical Mycoplasma lipophilum cluster (Weisburg et al. 1989) and description of two new clusters in the hominis group based on 16S rDNA sequences, Int'l Journal of Systematic & Evolutionary Microbiology (2001) vol. 51, pp. 633-643.

Sarah A. Lewis et al., "Association of Specific allergen sensitization with socioeconomic factors and allergic disease in a population of Boston women", J. Allergy Clin. Immunol., vol. 107, No. 4, Apr. 2001, pp. 615-622.

Katherine A. Lyseng-Williamson et al., "Inhaled Salmeterol/Fluticasone Propionate Combination in Chronic Obstructive Pulmonary Disease," Am. J. Respir. Med. vol. 1, No. 4, 2002, pp. 273-282.

Jeffrey W. Millard et al., "Solubilization by cosolvents Establishing useful constants for the log-linear model," Int'l Journal of Pharmaceutics vol. 245, 2002, pp. 153-166.

C. Baumgarten et al., "Initial Treatment of Symptomatic Mild to Moderate Bronchial Asthma with the Salmeterol/Fluticasone Propionate (50/250µg) Combination Product (SAS 40023)" European Journal of Medical Research 2002, vol. 7, pp. 1-7.

Stephen J. Fowler et al., "Step-down therapy with low-dose fluticasone-salmeterol combination or medium-dose hydrofluoroalkane 134a-beclomethasone alone" J. Allergy Clin. Immunol., vol. 109, No. 6, Jun. 2002, pp. 929-935.

Elizabeth F. Juniper et al., "Impact of Inhaled Salmeterol/Fluticasone Propionate Combination Product versus Budesonide on the Health-Related Quality of Life of Patients with Asthma," Am. J. Respir. Med., vol. 1, No. 6, 2002, pp. 435-440.

William Busse et al., "Steroid-sparing effects or fluticasone propionate 100 µg and salmeterol 50 µg administered twice daily in a single product in patients previously controlled with fluticaasone propionate 250 µg administered twice daily" J. Allergy Clin. Immunol., vol. 111, No. 1, Jan. 2003, pp. 57-65.

Ueno H Et Al, "Synthesis And Evaluation Of Anti-inflammatory Activities Of A Series Of Corticosteroid 17. Alpha—Esters Containing A Functional Group", Journal Of Medicinal Chemistry, American Chemical Society, vol. 34, No. 8, Aug. 1991, pp. 2468-2473.

Peter J Barnes, "Novel approaches and targets for treatment of Chronic Obstructive Pulmonary Disease" American Journal Of Respiratory And Critical Medicine, vol. 160, 1999, S72-S79.

B.J O Conner: "Combination Therapy", Pulmonary Pharmacology And Therapeutics, vol. 11, No. 5/6, 1998, pp. 397-399.

Peter J Barnes, "Chronic Obstructive Pulmonary Disease: New Opportunities For Drug Development" Trends In Pharmacological Sciences, Elsevenir Trends Journal, vol. 19, No. 10, 1998, pp. 415-423.

Simon Bowler, "Long Acting Beta Agonists", Austrailian Family Physician,vol. 27, No. 12, 1998, pp. 1114-1118.

Naedle-Risha R et al, "Dual Components Of Optimal Asthma Therapy: Scientific And Clinical Rationale For The Use Of Long Acting Beta-Agonists With Inhaled Corticosteroids", The Journal Of The American Osteopathic Association, vol. 101, No. 9, Sep. 2001, pp. 2001-2009.

T Van Der Molen et al, "Effects Of The Long Acting Beta Agonist Formoterol On Asthma Control In Asthmatic Patients Using Inhaled Corticosteroids", vol. 52, No. 6, 1997, pp. 535-539.

B.N. Lutsky et al, "A Novel Class of potent Topical Anti-inflammatory Agents: 17 Benzoylated, 7—Halogeno Substituted Corticosteroids", Arzeneimittel Forschung, vol. 29, No. 11, Nov. 1979, pp. 1662-1667.

Peter J. Barnes, "Efficacy of Inhaled Corticosteroids in Asthma", The Journal of Allergy and Clinical Immunology, vol. 102, No. 4, pp. 531-538.

U.S. Appl. No. 10066964, filed Feb. 4, 2002.
U.S. Appl. No. 10/067,010, filed Feb. 4, 2002.
U.S. Appl. No. 10/066,836, filed Feb. 4, 2002.
U.S. Appl. No. 10/200,364, filed Jul. 22, 2002.
U.S. Appl. No. 10/281,735, filed Oct. 28, 2002.
U.S. Appl. No. 10/241,658, filed Sep. 11, 2002.
U.S. Appl. No. 10/067,020, filed Feb. 4, 2002.
U.S. Appl. No. 09/958,050, filed Oct. 2, 2001.

Li, et al., Synthesis of aryl 5-(2-chlorophenyl)-2-furoates under phase transfer catalysis, Synthetic Communications 32 (20): 3081-3086 (2002).

Tanaka et al., "Synthesis of 4H-furo[3,2-b]indole derivatives. III (1). Preparation of 4H-furo[3,2-b]indole-2-carboxylic acid derivatives," Journal Heterocyclic Chemistry 16:785-788 (1979).

Moreno-Vargas et al., Synthesis and glycosidase inhibitory activities of 5-(1',4'-dideoxy-1',4'-imino-D-erthrosyl)-2-methyl-3-furoic acid (=5-[3S,4R)-3,4-dihyrdoxypyrrolidin-2-yl]-2methylfuran-3-carboxylic acid) derivatives: New leads as selective a-L-fucosidase and B-galactosidase inhibitors,) Helvetica Chimica Acta 86:1894-1913 (2003).

Wenkert et al., "Short syntheses of furan and catechol derivatives. A synthesis of hydrourushiol 1,2," Journal American Chemical Society 105; 2021-2029 (1983).

Kooreman et al., "The synthesis of 17-esters of corticosteroids protection of 11B-hydroxyl of the trimethylsilyl group," Synthetic Communications 1(2): 81-87 (1971).

Chapman et al; "Anti-Inflammatory Activity of Inhaled Mometasone Furoate in Allergic Mice"; Ameim-Forsch/Drug Res; 1998; 48(4); 384-391.

Lutsky, et al; "A Novel Class of Potent Topical Antiinflammatory Agents: 17-Benzolylated, 7a-Halogeno Substituted Corticosteroids"; Arzneim.-Forsch./Drug Res.; 1979; 29(11); 1662-1667.

Togashi et al.; 9-fluoro-11B, 17, 21-trihyrdroxy-16a-methyl-1,4-pregnadiene-3, 20-dione 21-cyclohexanecarboxylate 17-cyclopropanecarboxylate (ST126); Oyo Yakuri; (2002); 63(5/6); 61-77.

William R. Lumry, MD; "A review of the preclinical and clinical data of newer intranasal steroids used in the treatment of allergic rhinitis"; J. Allergy Clin. Immunol.; Oct. 1999, 104(4 Pt 1); S150-158.

Onrust, et al.; "Mometasone Furoate: A Review of its Intranasal Use in Allergic Rhinitis"; Drugs; Oct. 1998; 56(4); 725-745.

Smith, et al. In vitro Glucocorticoid Receptor Binding and Transcriptional Activation by Topically Active Glucocorticoids, Arzneimettelforschung, 1998, 48(II)(9), 956-60.

CAS Registry No. 102113-40-6.

Shapiro et al., "17-Esters and 17, 21-Diesters of 9a, 11B-Dichlorocorticoids. Synthesis and anti-inflammatory activity," Steroids 9(2): 143-156 (1967).

Shapiro et al., "Synthesis and structure-activity studies of corticosteroid 17-heterocyclic aromatic esters. 1. 9a, 11B dichloro series, "Journal of Medicinal Chemistry 30(6): 1068-1073 (1987).

Sakagami et al, "Mucoadhexive BDP microspheres for powder inhalation-their unique pharmacokinetic-pharmacodynamic profiles," Respiratory Drug Delivery VI, pp. 193-199 (1998).

PCT/GB01/03495 Written Opinion, date of mailing Apr. 4, 2002.

PCT/GB01/03495 International Preliminary Examination Report, date of mailing Aug. 30, 2002.

Pharmacokinetics of GW685698X and CC118781 (Fluticasone Propionate) when Co-Administered by the Intratracheal or Intravenous Route to the Anaesthetised White Pig (Study No. 03DMW062). The Pharmacokinetics of GW685698X and CC118781 Following Intratracheal Co-Administration to the Anaesthetised White Pig (Study No. B30947).

"Fluticasone"; CAS Registry No. 90566-53-3; 1984.

Definition of "Fluticasone"; Dictionary of Organic Compounds, 6th ed.; 1996; vol. 1; p. 3234.

Szefler et al.; "Chapter 21, Glucocorticoids in Severe Asthma: Mechanisms of Action and Route of Administration"; Difficult Asthma; 1999; pp. 371-375.

Mollmann et al.; "Chapter 14: Pharmacokinetic-Pharmacodynamic Correlations of Corticosteroids"; Handbook of Pharmacokinetic/Pharmacodynamic Correlation; 1995; pp. 323-336.

"Physical Tests: No. 941 X-Ray Diffraction"; The United States Pharmacopoeia, 23rd ed.; 1995; pp. 1843-1844.

FORMULATION CONTAINING ANTI-INFLAMMATORY ANDROSTANE DERIVATIVES

CROSS-REFERENCE TO RELATED APPLICATIONS

This application is a Continuation of U.S. patent application Ser. No. 10/066,951, filed 4 Feb. 2002, which issued as U.S. Pat. No. 6,787,532, which was a Continuation-in-part of U.S. patent application Ser. No. 09/958,050 filed on 2 Oct. 2001, which issued as U.S. Pat. No. 7,101,866, which was a 35 USC 371 National Phase Application of International Patent Application No. PCT.GB01.03495 filed 3 Aug. 2001, which claims priority to United Kingdom Patent Application No. GB 0019172.6 filed 5 Aug. 2000.

FIELD OF THE INVENTION

The present invention relates to a pharmaceutical formulations containing anti-inflammatory and anti-allergic compound of the androstanes series and to processes for their preparation. The present invention also relates to therapeutic uses thereof, particularly for the treatment of inflammatory and allergic conditions.

BACKGROUND OF THE INVENTION

Glucocorticoids which have anti-inflammatory properties are known and are widely used for the treatment of inflammatory disorders or diseases such as asthma and rhinitis. For example, U.S. Pat. No. 4,335,121 discloses 6α, 9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern glucocorticoids are very much safer than those originally introduced, it remains an object of research to produce new molecules and formulations of old and new molecules which have excellent anti-inflammatory properties, with predictable pharmacokinetic and pharmacodynamic properties, with an attractive side effect profile, and with a convenient treatment regime.

We have now identified a novel glucocorticoid compound and formulation thereof which substantially meets these objectives. In particular we have invented a novel formulation suitable for intranasal and also inhaled administration of a novel glucocorticoid compound and other esters of fluticasone including fluticasone propionate.

Many millions of individuals suffer from seasonal and perennial allergic rhinitis worldwide. Symptoms of seasonal and perennial allergic rhinitis include nasal itch, congestion, runny nose, sneezing and watery eyes. Seasonal allergic rhinitis is commonly known as 'hay fever'. It is caused by allergens which are present in the air at specific times of the year, for example tree pollen during Spring and Summer. Perennial allergic rhinitis is caused by allergens which are present in the environment during the entire year, for example dust mites, mold, mildew and pet dander.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognised as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors. In the case of administration of glucocorticoids, the potential for any undesirable side effects should preferably be minimised.

SUMMARY OF THE INVENTION

Thus, according to one aspect of the invention, there is provided a pharmaceutical formulation comprising an aqueous carrier liquid having dissolved therein (a) an ester of fluticasone or a solvate thereof as medicament and (b) a solubilising agent for assisting the solubilisation of the medicament in the aqueous carrier liquid.

Preferably the ester of fluticasone is a compound of formula (I)

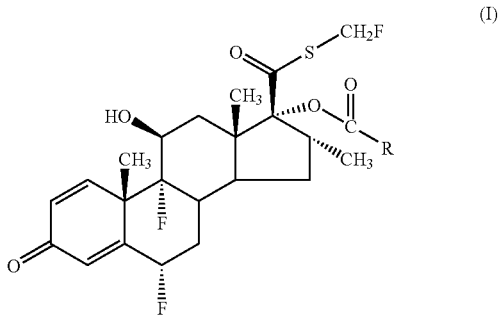

wherein R represents ethyl or a 5 membered heterocyclic aromatic ring containing 1 to 3 heteroatoms selected from O, N and S, optionally substituted by one or more methyl or halogen atoms or a solvate thereof.

Solvates of esters of fluticasone includes solvates with pharmaceutically acceptable solvents eg hydrates.

In a first embodiment of the invention, preferably R represents ethyl and the compound of formula (I) is fluticasone propionate.

In a second embodiment of the process, preferably R represents furan-2-yl and the compound of formula (I) has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester.

Hitherto, nasal formulations of glucocorticoid compounds, particularly aqueous formulations of glucocorticoid compounds, have been in the form of suspensions. In such suspension products the active ingredient is suspended in the aqueous carrier in the form of finely divided particles, typically of mass median diameter (MMD) 1-5 microns. Particles of this size are typically produced by micronisation, which is a wasteful and hazardous process.

Solution formulations have advantages in that the use of micronisation processes may be avoided and also in that onset of action may be increased since it is not necessary for any dissolution process to take place before the drug enters the cells in which it acts and exerts its anti-inflammatory effect. However fluticasone esters are quite insoluble in water (typically less than 1 μg/ml) and so it might be thought that the large volumes of dilute liquid which would need to be administered to have therapeutic effect would be impractical. We have now surprisingly discovered that the presence of a solubilising agent which is preferably a surfactant, especially a surfactant selected from the group consising of a α-[4-(1,1,3,3-tetramethylbutyl)phenyl]-ω-hydroxypoly(oxy-1,2-ethanediyl) polymer (also known as a octylphenoxypolyethoxyethanol) and a 4-(1,1,3,3-tetramethylbutyl)phenol polymer with formaldehyde and oxirane significantly increases the solubility of fluticasone esters in water thus permitting acceptably concentrated solutions to be developed. The solubility of fluticasone esters in water in the presence of such a surfactant is maximised when the formulation is prepared in a particular manner as described later which forms a particular aspect of the invention.

We have also surprisingly discovered that the solubility of fluticasone esters can be increased yet further by dissolution in the aqueous carrier liquid of a hydroxyl containing organic co-solvating agent or of phosphatidiyl choline. Thus formulations including this additional component have further advantages and are preferred.

Examples of α-[4-(1,1,3,3-tetramethylbutyl)phenyl]-ω-hydroxypoly(oxy-1,2-ethanediyl) polymer surfactants include those of the Triton series eg Triton X-100, Triton X-114 and Triton X-305 in which the X number is broadly indicative of the average number of ethoxy repeating units in the polymer. For example the average number of ethoxy repeating units in a series of Triton X surfactants is as follows:

| Triton | Average number of ethoxy units |
|---|---|
| X-45 | 5 |
| X-114 | 7-8 |
| X-100 | 9-10 |
| X-102 | 12-13 |
| X-165 | 16 |
| X-305 | 30 |
| X-405 | 40 |
| X-705 | 70 |

Preferably the number of repeating units in the α-[4-(1,1,3,3-tetramethylbutyl)phenyl]-ω-hydroxypoly(oxy-1,2-ethanediyl) polymer is around 7-70, particularly around 7-30 especially around 7-10.

4-(1,1,3,3-Tetramethylbutyl)phenol polymers with formaldehyde and oxiran typically have a relative molecular weight of 3500-5000 especially 4000-4700. An example structure is given below:

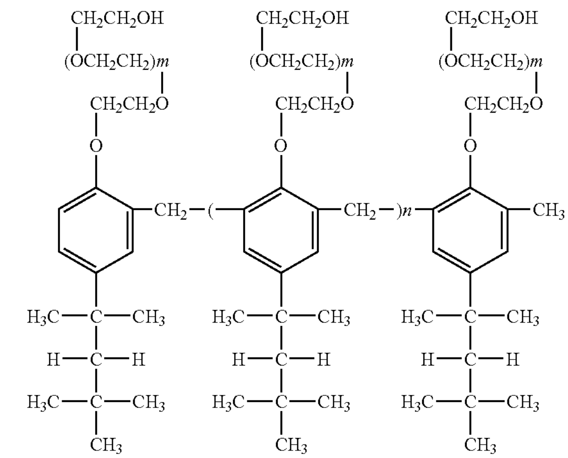

m = 6-8
n ≤ 5
Form = 7 and n = 5, MW is 4,326

Thus as just noted, m may represent 6-8 eg 7 and n may represent 1-5, especially 3-5 eg 5. The preferred example is Tyloxapol.

Preferably the surfactant is Triton X-100 or Tyloxapol since these surfactants have the highest solubilising power and can therefore be employed at the lowest concentrations. The most preferred surfactant is Tyloxapol.

The solubility of fluticasone propionate in various surfactants in water with and without an organic co-solvating agent or phosphatidyl choline is given in the following table:

| Surfactant | Concentration (% w/w) | Solubility (μg/ml) |
|---|---|---|
| Triton X-100 | 2 | 69 |
| Tyloxapol | 2 | 41 |
| Tyloxapol | 5 | 133 |
| Tyloxapol and | 5 | 197 |
| Phospatidyl choline | 1 | |
| Tyloxapol and | 5 | 207 |
| PEG200 | 10 | |
| Labrasol | 10 | None detected |
| Sodium chenodesoxycholate | 5 | 5.9 |
| Triton X-45 | 5 | None detected |
| Sodium cholate | 20 | 140 |
| | 2 | 11 |
| — | — | <1 |

Labrasol, sodium chenodesoxycholate, Triton X-45 and sodium cholate were not considered suitable for use in formulations according to the invention since excessively high concentrations of such surfactants are needed to be used to dissolve the fluticasone ester to a sufficient extent.

The solubility in water of compound of formula (I) in which R represents furan-2-yl in various surfactants is shown in the following table:

| Surfactant | Concentration (% w/w) | Solubility (μg/ml) |
|---|---|---|
| Triton X-100 | 0.5 | 18 |
| " | 2 | 266 |
| " | 5 | 549 |
| Triton X-100 and | 5 | 840 |

-continued

| Surfactant | Concentration (% w/w) | Solubility (μg/ml) |
|---|---|---|
| PEG200 | 10 | |
| Tyloxapol | 2 | 95 |
| " | 5 | 307 |
| " | 6 | 346 |
| " | 7.5 | 576 |
| " | 10 | 585 |
| Triton X-305 | 5 | 204 |
| — | — | <1 |

In formulations of the invention, the surfactant will typically be employed in a concentration of around 0.5-10%, preferably around 2-5% w/w based on weight of formulation. The precise concentration chosen will depend on the nature and concentration of the glucorticoid. The surfactant will need to be soluble in the formulation at the concentration used.

Examples of hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is also preferably avoided.

The hydroxyl containing organic co-solvating agents are typically employed at a concentration of 1-20% eg 5-10%, eg around 5% w/w based on weight of formulation.

When phosphatidyl choline is employed it is typically employed at a concentration of 0.1-10% eg 0.5-5%, eg around 1% w/w based on weight of formulation.

The effect of addition of a hydroxyl containing organic co-solvating agent to solubility in water of compound of formula (I) in which R represents furan-2-yl in various surfactants is shown in the following table:

| Surfactant/ co-solvating agent | Concentration (% w/w) | Solubility (μg/ml) |
|---|---|---|
| Tyloxapol | 5 | 344 |
| Tyloxapol | 5 | 836 |
| PEG200 | 10 | |
| Tyloxapol | 5 | 422 |
| Propylene glycol | 10 | |
| Tyloxapol | 5 | 526 |
| Dextrose | 4 | |

The aqueous carrier liquid will essentially comprise water.

However for nasal administration it may also have dissolved in it one or more of the following components:
viscosity enhancing agents.
preservatives.
isotonicity adjusting agents.

The formulations of the present invention may be stabilised by appropriate selection of pH using hydrochloric acid. Typically, the pH will be adjusted to between 4.5 and 7.5, preferably between 5.0 and 7.0, especially around 6.5.

Examples of pharmaceutically acceptable materials which can be used to adjust the pH of the formulation include hydrochloric acid and sodium hydroxide. Preferably, the pH of the formulation will be adjusted using hydrochloric acid.

The aqueous component is preferably a high grade quality of water, most preferably purified water.

Examples of viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols. Preferably, the viscosity enhancing agent will be carboxy methylcellulose sodium.

Preferably, the viscosity enhancing agent will possess thixotropic properties which will ensure that the formulation assumes a gel like appearance at rest, characterised by a high viscosity value. Once the composition is subjected to shear forces, such as those caused by agitation prior to spraying, the viscosity of the formulation will preferably decrease transiently to such a level to enable it to flow readily through the spray device and exit as a fine mist spray. This mist will then be capable of infiltrating the mucosal surfaces of the anterior regions of the nose (frontal nasal cavities), the frontal sinus, the maxillary sinuses and the turbinates which overlie the conchas of the nasal cavities. Once deposited, the viscosity of the formulation will preferably increase to a sufficient level to assume its gel-like form and resist being cleared from the nasal passages by the inherent mucocillary forces that are present in the nasal cavities.

When the formulation of the present invention comprises a viscosity enhancing agent, it will be desirably added in a suitable amount to achieve this function, preferably the viscosity enhancing agent will be present within the formulation in an amount of between 0.1 and 5% (w/w), eg 1.5% (w/w), based on the total weight of the formulation.

For stability purposes, the formulation of the present invention should be protected from microbial contamination and growth. Examples of pharmaceutically acceptable anti-microbial agents that can be used in the formulation include quaternary ammonium compounds (eg. benzalkonium chloride, benzethonium chloride, cetrimide and cetylpyridinium chloride), mercurial agents (eg. phenylmercuric nitrate, phenylmercuric acetate and thimerosal), alcoholic agents (eg. chlorobutanol, phenylethyl alcohol and benzyl alcohol), antibacterial esters (eg. esters of para-hydroxybenzoic acid), chelating agents such as disodium edetate (EDTA) and other anti-microbial agents such as chlorhexidine, chlorocresol, sorbic acid and its salts and polymyxin.

Preferably, the preservative will comprise disodium edetate, which will preferably be present within the formulation in an amount of between 0.001 and 1% (w/w), especially around 0.015% (w/w), based on the total weight of the formulation.

Preferably the preservative will comprise potassium sorbate which will preferably be present within the formultaion in an amount of between 0.01 and 1% (w/w), especially around 0.015% (w/w) based on the total weight of the formulation.

Preferably, the preservative will comprise benzalkonium chloride (BKC), which will preferably be present within the formulation in an amount of between 0.001 and 1% (w/w), especially around 0.015% (w/w), based on the total weight of the formulation.

More preferably, the preservative comprises disodium edetate and benzalkonium chloride.

The presence of an isotonicity adjusting agent is to achieve isotonicity with body fluids eg fluids of the nasal cavity, resulting in reduced levels of irritancy associated with many nasal formulations. Examples of suitable isotonicity adjusting agents are sodium chloride, dextrose and calcium chloride. Preferably, the isotonicity adjusting agent will be dextrose, most preferably used as dextrose anhydrous.

When the formulation of the present invention comprises an isotonicity adjusting agent it will be desirably added in a sufficient quantity to achieve this function, preferably the isotonicity adjusting agent will be present within the formulation in an amount of between 0.1 and 10% (w/w), especially 5.0% w/w, based on the total weight of the formulation.

Fluticasone esters eg the compounds of formula (I), especially when R represents furan-2-yl, and formulations thereof have potentially beneficial anti-inflammatory or anti-allergic effects, particularly upon topical administration to the nose, demonstrated by, for example, its ability to bind to the glucocorticoid receptor and to illicit a response via that receptor, with long acting effect. Hence, formulations according to the invention are useful in the treatment of inflammatory and/or allergic disorders of the nose, especially in once-per-day therapy.

Formulations according to the invention may be prepared by dissolving the ingredients in water. If necessary the pH may be adjusted as a final step. Generally it will be desirable to filter the solution to remove any residual particulate matter. Formulations so prepared may then be filled into the receptacle.

We have however invented an improved process for preparing formulations according to the invention which comprises:
(a) dissolving the fluticasone ester in the undiluted surfactant at an elevated temperature (typically 60-70° C.);
(b) adding hot water (typically 60-70° C.) together with other formulation ingredients to achieve the desired concentration of active ingredient;
(c) if desired modifying the pH of the final solution;
(d) filtering the hot solution to remove any residual particulate matter.

Preferably the temperature of the liquids in steps (a) and (b) and the temperature of the liquid filtered in step (c) is 45° C. or greater, preferably 55° C. or greater, especially 65° C. or greater. The temperature is preferably 80° C. or less, eg 70° C. or less.

As noted above, this improved process permits solutions of higher concentration to be prepared than is possible by conventional techniques. For example this process performed at 60-70° C. increases the solubility of fluticasone propionate from 87 to 133 µg/ml in 5% Tyloxapol and the compound of of formula (I) when R represents furan-2-yl from 233 to 344 µg/ml in 5% Tyloxapol relative to the process performed at room temperature.

Aqueous formulations of the invention may also be employed for rectal, aural, otic, oral, topical or parenteral administration or administration by inhalation for the treatment of other local inflammatory conditions (eg dermatitis, asthma, chronic obstructive pulmonary disease (COPD) and the like). For example formulations of the invention may be administered to the lung by nebulisation. Such formulations may employ excipients (eg preservatives, buffers and the like) appropriate for the route of administration.

The particularly desirable biological properties of the compound of formula (I) wherein R represents furan-2-yl are now explained below:

Compound (I) wherein R represents furan-2-yl undergoes highly efficient hepatic metabolism to yield the 17-β carboxylic acid (X) as the sole major metabolite in rat and human in vitro systems. This metabolite has been synthesised and demonstrated to be >1000 fold less active than the parent compound in in vitro functional glucocorticoid assays.

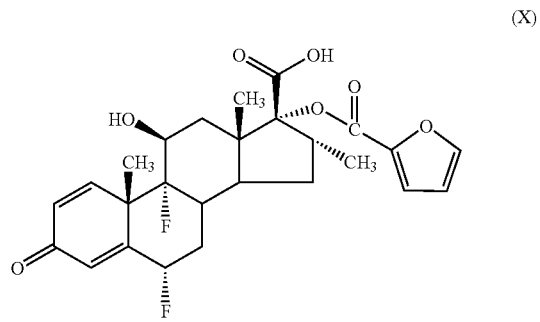

(X)

This efficient hepatic metabolism is reflected by in vivo data in the rat, which have demonstrated plasma clearance at a rate approaching hepatic blood flow and an oral bioavailability of <1%, consistent with extensive first-pass metabolism.

In vitro metabolism studies in human hepatocytes have demonstrated that compound (I) is metabolised in an identical manner to fluticasone propionate but that conversion of (I) to the inactive acid metabolite occurs approximately 5-fold more rapidly than with fluticasone propionate. This very efficient hepatic inactivation would be expected to minimise systemic exposure in man leading to an improved safety profile.

Inhaled glucocorticoids are also absorbed through the lung and this route of absorption makes a significant contribution to systemic exposure. Reduced lung absorption could therefore provide an improved safety profile. Studies with compound (I) have shown significantly lower exposure to compound (I) than with fluticasone propionate after dry powder delivery to the lungs of anaesthetised pigs.

Examples of disease states in which fluticasone esters have utility include inflammatory and/or allergic conditions of the nasal passages such as rhinitis eg seasonal and perennial rhinitis as well as other local inflammatory conditions such as asthma, COPD and dermatitis.

It will be appreciated by those skilled in the art that reference herein to treatment extends to prophylaxis as well as the treatment of established conditions.

Preferable means for applying the formulation of the present invention to the nasal passages is by use of a pre-compression pump. Most preferably, the pre-compression pump will be a VP7 model manufactured by Valois SA. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a botte capable of holding 10-50 ml of a formulation. Each spray will typically deliver 50-100 µl of such a formulation, therefore, the VP7 model is capable of providing at least 100 metered doses.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

Typically, one or two inhalations per nostril would be administered by the above procedure up to three times each day, preferably once or twice daily especially once daily.

It will be appreciated that the above dosing regime should be adjusted according to the patient's age, body weight and/or symptom severity.

As mentioned above, formulations comprising a fluticasone esters are useful in human or veterinary medicine, in particular as an anti-inflammatory and anti-allergic agent.

There is thus provided as a further aspect of the invention a formulation comprising the fluticasone ester or a physiologically acceptable solvate thereof for use in human or veterinary medicine, particularly in the treatment of patients with inflammatory and/or allergic conditions.

According to another aspect of the invention, there is provided the use of a formulation comprising the fluticasone ester or physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a formulation comprising the fluticasone ester or physiologically acceptable solvate thereof.

Further, there is provided a process for the preparation of such pharmaceutical compositions which comprises mixing the ingredients.

The proportion of the active fluticasone ester in the local compositions according to the invention depends on the precise type of formulation to be prepared but will generally be within the range of around 0.001-12%, more preferably 0.001 to 10% by weight. Generally, however for most types of preparations advantageously the proportion used will be within the range of from 0.001 to 1%, more preferably 0.001-0.5, and especially around 0.005 to 0.1%.

The compound of formula (I) wherein R represents furan-2-yl is long-acting, therefore preferably the compound will be delivered once-per-day and the dose will be selected so that the compound has a therapeutic effect in the treatment of respiratory disorders (eg rhinitis) over 24 hours or more.

The pharmaceutical compositions according to the invention may also be used in combination with another therapeutically active agent, for example, an anti-histamine or an anti-allergic. The invention thus provides, in a further aspect, a combination comprising the fluticasone ester or a physiologically acceptable solvate thereof together with another therapeutically active agent, for example, an anti-histamine or an anti-allergic.

Examples of anti-histamines include methapyrilene or loratadine.

Other suitable combinations include, for example, other anti-inflammatory agents eg NSAIDs (eg sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (eg antibiotics, antivirals).

Also of particular interest is use of the fluticasone ester or a physiologically acceptable solvate thereof in combination with a phosphodiesterase 4 (PDE4) inhibitor eg cilomilast or a salt thereof.

For administration to the lung, the pharmaceutical compositions according to the invention may also be used in combination with a $\beta_2$ adrenoreceptor agonist. Examples of $\beta_2$-adrenoreceptor agonists include salmeterol (eg as racemate or single enantiomer such as the s-enantiomer), salbutamol, formoterol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period.

Since the compounds of formula (I) are long-acting, preferably a composition comprising the compound of formula (I) and the long-acting $\beta_2$-adrenoreceptor agonists will be delivered once-per-day and the dose of each will be selected so that the composition has a therapeutic effect in the treatment of respiratory disorders effect (eg in the treatment of asthma or COPD, particularly asthma) over 24 hours or more.

Further, there is provided a process for the preparation of such pharmaceutical compositions which comprises mixing the ingredients.

The individual compounds of such combinations may be administered either sequentially in separate pharmaceutical compositions as well as simultaneously in combined pharmaceutical formulations. Preferably additional therapeutically active ingredients are dissolved in the formulation together with the fluticasone ester. Appropriate doses of known therapeutic agents will be readily appreciated by those skilled in the art.

Fluticasone esters may generally be prepared following the methods of GB2088877B and Phillips et al (1994) J Med Chem, 37, 3717-3729.

For example, a process for preparing a compound of formula (I) and other fluticasone esters comprises alkylation of a thioacid of formula (II)

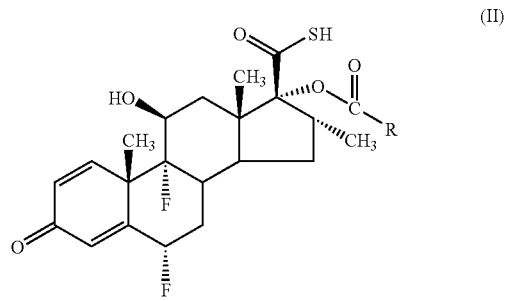

or a salt thereof.

In this process the compound of formula (II) may be reacted with a compound of formula $FCH_2L$ wherein L represents a leaving group (eg a halogen atom, a mesyl or tosyl group or the like) for example, an appropriate fluoromethyl halide under standard conditions. Preferably, the fluoromethyl halide reagent is bromofluoromethane. Preferably the compound of formula (II) is employed as a salt, particularly the salt with diisopropylethylamine.

In a preferred process for preparing the compound of formula (I), the compound of formula (II) or a salt thereof is treated with bromofluoromethane optionally in the presence of a phase transfer catalyst. A preferred solvent is methylacetate, or more preferably ethylacetate, optionally in the presence of water. The presence of water improves solubility of both starting material and product and the use of a phase transfer catalyst results in an increased rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF has also successfully been employed as solvent for the reaction wherein the presence of a phase transfer catalyst again provides a significantly faster reaction rate. Preferably the product present in an organic phase is washed firstly with aqueous acid eg dilute HCl in order to remove amine compounds such as triethylamine and diisopropylethylamine and then with aqueous base eg sodium bicarbonate in order to remove any unreacted precursor compound of formula (II).

Compound of formula (I) wherein R represents furan-2-yl in unsolvated form may be prepraed by a process comprising:
(a) Crystallising the compound of formula (I) in the presence of a non-solvating solvent such as ethanol, methanol, water, ethyl acetate, toluene, methylisobutylketone or mixtures thereof; or
(b) Desolvating a compound of formula (I) in solvated form (eg in the form of a solvate with acetone, isopropanol, methylethylketone, DMF or tetrahydrofuran) eg by heating.

In step (b) the desolvation will generally be performed at a temperature exceeding 50° C. preferably at a temperature exceeding 100° C. Generally heating will be performed under vacuum.

Compound of formula (I) wherein R represents furan-2-yl has been prepared in three crystalline polymorphic forms designated Form 1, Form 2 and Form 3 which are distinguishable by their X-ray powder diffraction (XRPD) profiles. Form 3 appears to be an unstable variant of Form 2. Form 1 appears to be the thermodynamically most stable form and is therefore preferred.

A process for preparing a compound of formula (I) as unsolvated Form 1 polymorph comprises dissolving compound of formula (I) in methylisobutylketone, ethyl acetate or methyl acetate and producing compound of formula (I) as unsolvated Form 1 by addition of a non-solvating anti-solvent such as iso-octane or toluene.

According to a first preferred embodiment of this process the compound of formula (I) may be dissolved in ethyl acetate and compound of formula (I) as unsolvated Form 1 polymorph may be obtained by addition of toluene as anti-solvent. In order to improve the yield, preferably the ethyl acetate solution is hot and once the toluene has been added the mixture is distilled to reduce the content of ethyl acetate.

According to a second preferred embodiment of this process the compound of formula (I) may be dissolved in methylisobutylketone and compound of formula (I) as unsolvated Form 1 polymorph may be obtained by addition of isooctane as anti-solvent Compound of formula (I) in solvated form may be prepared by crystallising the compound of formula (I) from a solvating solvent such as acetone or tetrahydrofuran (THF).

Compounds of formula (II) may be prepared from the corresponding 17α-hydroxyl derivative of formula (III):

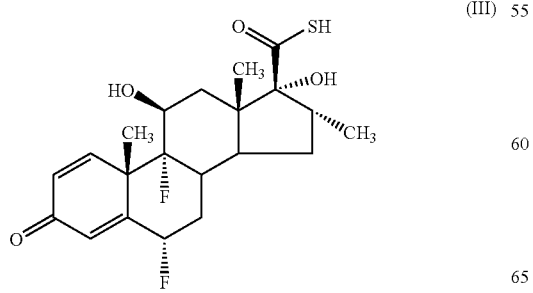

(III)

using for example, the methodology described by G. H. Phillipps et al., (1994) Journal of Medicinal Chemistry, 37, 3717-3729. For example the step typically comprises the addition of a reagent suitable for performing the esterification eg an activated derivative of RCOOH such as an activated ester or preferably an acid halide eg RCOOCl (employed in at least 2 times molar quantity relative to the compound of formula (III)) in the presence of an organic base eg triethylamine. The second mole of RCOOCl reacts with the thioacid moiety in the compound of formula (III) and needs to be removed eg by reaction with an amine such as diethylamine.

This method suffers disadvantages, however, in that the resultant compound of formula (II) is not readily purified of contamination with the by-product RCON(Et)₂ We have therefore invented several improved processes for performing this conversion.

In a first such improved process we have discovered that by using a more polar amine such as diethanolamine, a more water soluble by-product is obtained (in this case RCO-diethanolamide) which permits compound of formula (II) or a salt thereof to be produced in high purity since the by-product can efficiently be removed by water washing.

A process for preparing a compound of formula (II) comprises:
(a) reacting a compound of formula (III) with an activated derivative of RCOOH as in an amount of at least 2 moles of the activated derivative per mole of compound of formula (III) to yield a compound of formula (IIA)

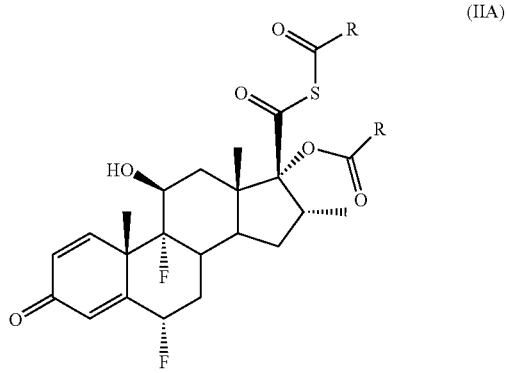

(IIA)

; and
(b) removal of the sulphur-linked R—CO— moiety from compound of formula (IIA) by reaction of the product of step (a) with an organic primary or secondary amine base capable of forming a water soluble amide.

In two particularly convenient embodiments of this process we also provide methods for the efficient purification of the end product which comprise either
(c1) when the product of step (b) is dissolved in a substantially water immiscible organic solvent, purifying the compound of formula (II) by washing out the amide by-product from step (b) with an aqueous wash, or
(c2) when the product of step (b) is dissolved in a water miscible solvent, purifying the compound of formula (II) by treating the product of step (b) with an aqueous medium so as to precipitate out pure compound of formula (II) or a salt thereof.

In step (a) preferably the activated derivative of RCOOH may be an activated ester of RCOOH, but is more preferably an acid halide, especially RCOOCl. A suitable solvent for this reaction is ethylacetate or methylacetate (preferably methylacetate) (when step (c1) may be followed) or acetone (when step (c2) may be followed). Normally an organic base eg triethylamine will be present. In step (b) preferably the organic base is diethanolamine. The base may suitably be dissolved in a solvent eg methanol. Generally steps (a) and (b) will be performed at reduced temperature eg between 0 and 5° C. In step (c1) the aqueous wash may be water, however the use of brine results in higher yields and is therefore preferred. In step (c2) the aqueous medium is for example a dilute aqueous acid such as dilute HCl.

An alternative process for preparing a compound of formula (II) comprises:

(a) reacting a compound of formula (III) with an activated derivative of RCOOH in an amount of at least 2 moles of activated derivative per mole of compound of formula (III) to yield a compound of formula (IIA); and (b) removal of the sulphur-linked RCO moiety from compound of formula (IIA) by reaction of the product of step (a) with a further mole of compound of formula (III) to give two moles of compound of formula (II).

In step (a) preferably the activated derivative of RCOOH may be an activated ester of RCOOH, but is more preferably an acid halide, especially RCOOCl. A suitable solvent for his step is acetone. Normally an organic base eg triethylamine will be present. In step (b) a suitable solvent is DMF or dimethylacetamide. Normally an organic base eg triethylamine will be present. Generally steps (a) and (b) will be performed at reduced temperature eg between 0 and 5° C. The product may be isolated by treatment with acid and washing with water.

This aforementioned process is very efficient in that it does not produce any amide by-product (thus affording inter alia environmental advantages) since the excess mole of ester moiety is taken up by reaction with a further mole of compound of formula (II) to form an additional mole of compound of formula (II).

Further general conditions for the conversion of compound of formula (III) to compound of formula (II) in the two processes just described will be well known to persons skilled in the art.

We have found that the compound of formula (II) may advantageously be isolated in the form of a solid crystalline salt. The preferred salt is a salt formed with a base such as triethylamine, 2,4,6-trimethylpyridine, diisopropylethylamine or N-ethylpiperidine. Such salt forms of compound of formula (II) are more stable, more readily filtered and dried and can be isolated in higher purity than the free thioacid. The most preferred salt is the salt formed with diisopropylethylamine. The triethylamine salt is also of interest.

Compounds of formula (III) may be prepared in accordance with procedures described in GB 2088877B.

Compounds of formula (III) may also be prepared by a process comprising the following steps:

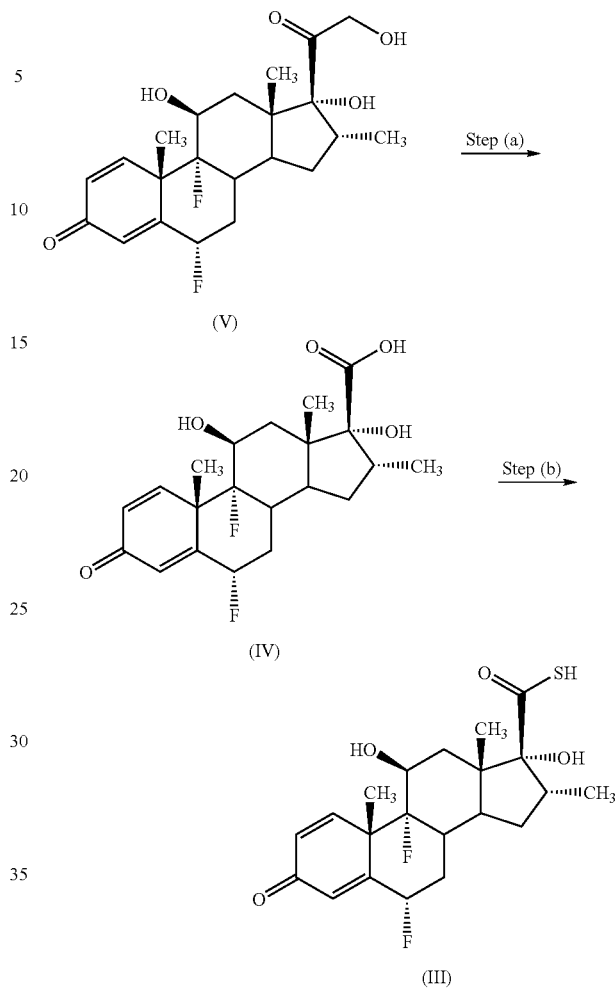

Step (a) comprises oxidation of a solution containing the compound of formula (V). Preferably, step (a) will be performed in the presence of a solvent comprising methanol, water, tetrahydrofuran, dioxan or diethylene glygol dimethylether. So as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1-9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (IV) may be isolated by recrystallisation from the reaction mixture by addition of an anti-solvent. A suitable anti-solvent for compound of formula (IV) is water. Surprisingly we have discovered that it is highly desirable to control the conditions under which the compound of formula (IV) is precipitated by addition of anti-solvent eg water. When the recrystallisation is performed using chilled water (eg water/ice mixture at a temperature of 0-5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice. By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no solvated solvent within the crystal lattice.

Step (b) will typically comprise the addition of a reagent suitable for converting a carboxylic acid to a carbothioic acid eg using hydrogen sulphide gas together with a suitable coupling agent eg carbonyldiimidazole (CDI) in the presence of a suitable solvent eg dimethylformamide.

The advantages of the formulation of the fluticasone esters according to the invention may include the fact that the formulations demonstrate excellent anti-inflammatory properties, with predictable pharmacokinetic and pharmacodynamic behaviour, with an attractive side-effect profile, rapid onset of action, long duration of action, and are compatible with a convenient regime of treatment in human patients, in particular being amendable to once-per day dosing. Further advantages may include the fact that the formulation has desirable physical and chemical properties which allow for ready manufacture and storage.

DETAILED DESCRIPTION OF THE INVENTION

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), ddd (doublet of doublet of doublets), dt (doublet of triplets) and b (broad). Biotage refers to prepacked silica gel cartridges containing KP-Sil run on flash 12i chromatography module. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).

INTERMEDIATES

Intermediate 1

6α, 9α-Difluoro-17α-[(2-furanylcarbonyl)oxy]-11β-hydroxy-16α-methyl-3-oxo-androsta-1, 4-diene-7β-carbothioic acid diisopropylethylamine salt A stirred suspension of 6α, 9α-difluoro-11β, 17α-dihydroxy-16α-methyl-3-oxo-androsta-1,4-diene-17β-carbothioic acid (prepared in accordance with the procedure described in GB 2088877B) (49.5 g) in methylacetate (500 ml) is treated with triethylamine (35 ml) maintaining a reaction temperature in the range 0-5° C. 2-Furoyl chloride (25 ml) is added and the mixture stirred at 0-5° C. for 1 hour. A solution of diethanolamine (52.8 g) in methanol (50 ml) is added and the mixture stirred at 0-5° C. for at least 2 hours. Dilute hydrochloric acid (approx 1M, 550 ml) is added maintaining a reaction temperature below 15° C. and the mixture stirred at 15° C. The organic phase is separated and the aqueous phase is back extracted with methyl acetate (2×250 ml). All of the organic phases are combined, washed sequentially with brine (5×250ml) and treated with di-isopropylethylamine (30 ml). The reaction mixture is concentrated by distillation at atmospheric pressure to an approximate volume of 250 ml and cooled to 25-30° C. (crystallisation of the desired product normally occurs during distillation/subsequent cooling). Tertiary butyl methyl ether (TBME) (500 ml) is added, the slurry further cooled and aged at 0-5° C. for at least 10 minutes. The product is filtered off, washed with chilled TBME (2×200 ml) and dried under vacuum at approximately 40-50° C. (75.3 g, 98.7%). NMR (CDCl$_3$) δ: 7.54-7.46 (1H, m), 7.20-7.12 (1H, dd), 7.07-6.99 (1H, dd), 6.48-6.41 (2H, m), 6.41-6.32 (1H, dd), 5.51-5.28 (1H, dddd $^2J_{H-F}$ 50 Hz), 4.45-4.33(1H, bd), 3.92-3.73 (3H, bm), 3.27-3.14 (2H, q), 2.64-2.12 (5H, m), 1.88-1.71 (2H, m), 1.58-1.15 (3H, s), 1.50-1.38 (15H, m), 1.32-1.23 (1H, m), 1.23-1.15 (3H s), 1.09-0.99 (3H, d)

Intermediate 2

6α, 9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1

A mobile suspension of Intermediate 1 (12.61 g, 19.8 mmol) in ethyl acetate (230 ml) and water (50 ml) is treated with a phase transfer catalyst (benzyltributylammonium chloride, 10 mol %), cooled to 3° C. and treated with bromofluoromethane (1.10 ml, 19.5 mmol, 0.98 equivalents), washing in with prechilled (0° C.) ethyl acetate (EtOAc) (20 ml). The suspension is stirred overnight, allowing to warm to 17° C. The aqueous layer is separated and the organic phase is sequentially washed with 1M HCl (50 ml), 1% w/v NaHCO$_3$ solution (3×50 ml) and water (2×50 ml). The ethylacetate solution is distilled at atmospheric pressure until the distillate reaches a temperature of approximately 73° C. at which point toluene (150 ml) is added. Distillation is continued at atmospheric pressure until all remaining EtOAc has been removed (approximate distillate temperature 103° C.). The resultant suspension is cooled and aged at <10° C. and filtered off. The bed is washed with toluene (2×30 ml) and the product oven dried under vacuum at 60° C. to constant weight to yield the title compound (8.77 g, 82%) LCMS retention time 3.66 min, m/z 539 MH+, NMR δ(CDCl$_3$) includes 7.60 (1H, m), 7.18-7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2m), 4.48 (1H, m), 3.48 (1H, m), 1.55 (3H, s), 1.16 (3H, s), 1.06 (3H, d, J 7 Hz).

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

For the experiments in this section, compound of formula (I) was used as unsolvated Form 1 (Intermediate 2)

The functional assay was based on that described by K. P. Ray et al., Biochem J. (1997), 328, 707-715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which $EC_{50}$ values were estimated.

In this test the compound of formula (I) showed an $EC_{50}$ value of <1 nM.

The glucocorticoid receptor (GR) can function in at least two distinct mechanisms, by upregulating gene expression through the direct binding of GR to specific sequences in gene promotors, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the firefly luciferase reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element, and which responds to direct stimulation by glucocorticoids. Simultaneous measurement of transactivation and transrepression was conducted by mixing the two cell lines in a 1:1 ratio in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added and after a further 15 hours at 37° C., the levels of firefly and renilla luciferase were measured using the Packard Firelite kit following the manufacturers' directions. Dose response curves were constructed from which $EC_{50}$ values were determined.

|  | Transactivation (GR) $ED_{50}$ (nM) | Transrepression (NFκB) $ED_{50}$ (nM) |
| --- | --- | --- |
| Compound of Formula (I) | 0.06 | 0.20 |
| Metabolite (X) | >250 | >1000 |
| Fluticasone propionate | 0.07 | 0.16 |

In Vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

For the experiments in this section, compound of formula (I) was used as unsolvated Form 1.

Compound of formula (I) produced dose dependant inhibition of lung eosinophilia in this model after dosing as an intra-tracheal (IT) suspension in saline 30 min prior to ovalbumin challenge. Significant inhibition is achieved after a single dose of 30 μg of compound of formula (I) and the response was significantly (p=0.016) greater than that seen with an equivalent dose of fluticasone propionate in the same study (69% inhibition with compound of formula (I) vs 41% inhibition with fluticasone propionate).

In a rat model of thymus involution 3 daily IT doses of 100 μg of compound (I) induced significantly smaller reductions in thymus weight (p=0.004) than an equivalent dose of fluticasone propionate in the same study (67% reduction of thymus weight with compound (I) vs 78% reduction with fluticasone propionate).

Taken together these results indicate a superior therapeutic index for compound (I) compared to fluticasone propionate.

In Vitro Metabolism in Rat and Human Hepatocytes

Incubation of compound (I) with rat or human hepatocytes shows the compound to be metabolised in an identical manner to fluticasone propionate with the 17-β carboxylic acid (X) being the only significant metabolite produced. Investigation of the rate of appearance of this metabolite on incubation of compound (I) with human hepatocytes (37° C., 10 μM drug concentration, hepatocytes from 3 subjects, 0.2 and 0.7 million cells/mL) shows compound (I) to be metabolised ca. 5-fold more rapidly than fluticasone propionate:

| Subject number | Cell density (million cells/mL) | 17-β acid metabolite production (pmol/h) | |
| --- | --- | --- | --- |
|  |  | Compound (I) | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102-118 pmol/h for compound (I) and 18.8-23.0 pmol/h for fluticasone propionate.

Pharmacokinetics after Intravenous (IV) and Oral Dosing in Rats

Compound (I) was dosed orally (0.1 mg/kg) and IV (0.1 mg/kg) to male Wistar Han rats and pharmacokinetic parameters determined. Compound (I) showed negligible oral bioavailability (0.9%) and plasma clearance of 47.3 mL/min/kg, approaching liver blood flow (plasma clearance of fluticasone propionate=45.2 mL/min/kg).

Pharmacokinetics after Intra-tracheal Dry Powder Dosing in the Pig.

Anaesthetised pigs (2) were dosed intra-tracheally with a homogenous mixture of compound (I) (1 mg) and fluticasone propionate (1 mg) as a dry powder blend in lactose (10% w/w). Serial blood samples were taken for up to 8 h following dosing. Plasma levels of compound (I) and fluticasone propionate were determined following extraction and analysis using LC-MS/MS methodology, the lower limits of quantitation of the methods were 10 and 20 pg/mL for compound (I) and fluticasone propionate respectively. Using these methods compound (I) was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for compound (I). This compensates for the plasma profile of Compound (I) only being defined up to 2 hours after an IT dose and removes any bias due to limited data between compound (I) and fluticasone propionate.

$C_{max}$ and AUC (0-inf) values show markedly reduced systemic exposure to compound (I) compared to fluticasone propionate:

|  | Cmax (pg/mL) | | AUC (0-inf) (hr · pg/mL) | |
| --- | --- | --- | --- | --- |
|  | Pig 1 | Pig 2 | Pig 1 | Pig 2 |
| Compound of Formula (I) | 117 | 81 | 254 | 221 |
| Fluticasone propionate | 277 | 218 | 455 | 495 |

The pharmacokinetic parameters for both compound (I) and fluticasone propionate were the same in the anaesthetised pig following intravenous administration of a mixture of the two compounds at 0.1 mg/kg. The clearance of these two glucocorticoids is similar is this experimental pig model.

Examples

Example 1

Nasal Formulation Containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester A formulation for intranasal delivery was prepared with ingredients as follows: 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester 0.005% w/w

| Tyloxapol | 2% w/w |
| --- | --- |
| dextrose | 5% w/w |
| BKC | 0.015% w/w |
| EDTA | 0.015% w/w |
| water | to 100% | in a total amount suitable for 120 actuations and the formulation was filled into a bottle (plastic or glass) fitted with a metering valve adapted to dispense 50 or 100 µl per actuation The device was fitted into a nasal actuator (Valois, e.g. VP3, VP7 or VP7D)

The formulation was prepared as follows:

The surfactant Tyloxapol was first heated to 60-70° C. to lower its viscosity. Intermediate 2 was then added very slowly while stirring using a suitable propellor mixer, while the surfactant was still hot. Separately, approximately 80% remaining quantity of water was heated similarly to 60-70° C., and dextrose dissolved completely using a propellor mixer. This solution, while still hot, was added very slowly to the drug/Tyloxapol solution while stirring. This preparation was allowed to continue mixing for a minimum of 30 min, or until all drug was observed to dissolve completely. In the remaining water, BKC and EDTA were dissolved and then added slowly to the final formulation, which was further mixed until clear. If still necessary, the formulation was brought to its final weight with water alone. The pH was determined, and adjusted to pH 6.5 if necessary.

Similarly prepared were other formulations as follows:

Example 2

Nasal Formulation Containing 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester A formulation for intranasal delivery was prepared with ingredients as follows: 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester 0.05% w/w

| Triton X-100 | 5% w/w |
| --- | --- |
| Dextrose | 4% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 µl per actuation. The device was fitted into a nasal actuator (Valois).

Example 3

Nasal Formulation Containing Fluticasone Propionate

A formulation for intranasal delivery was prepared with ingredients as follows:

| Fluticasone propionate | 0.05% w/w |
| --- | --- |
| Triton X-100 | 5% w/w |
| Dextrose | 4% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 µl per actuation.

Example 4

Nasal Formulation Containing Fluticasone Propionate

A formulation for intranasal delivery was prepared with ingredients as follows:

| | |
|---|---|
| Fluticasone propionate | 0.05% w/w |
| Tyloxapol | 5% w/w |
| dextrose | 5% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 µl per actuation The device was fitted into a nasal actuator (Valois).

Stability Testing

The chemical stability of Examples 1 and 2 was tested by placing samples at 5, 25 and 40° C. for a period 4 weeks and sampled as necessary. Analysis of the samples for drug content was done by HPLC.

| Example | Condition | Drug amount (% label) | EDTA (% w/w) | BKC (% w/w) | pH |
|---|---|---|---|---|---|
| Example 1 | Initial | 97.1 | 0.0151 | 0.0146 (97.0) | 6.70 |
| | 25° C./60% RH | 94.2 | 0.0149 | 0.0144 (95.6) | 6.20 |
| | 40° C./75% RH | 92.3 | 0.0145 | 0.0150 (99.8) | 5.82 |
| Example 2 | Initial | 100.4 | 0.0157 | 0.0161 (107.3) | 6.52 |
| | 25° C./60% RH | 96.4 | 0.0151 | 0.0135 (90.3) | 5.93 |
| | 40° C./75% RH | 95.4 | 0.0149 | 0.0144 (96.1) | 5.40 |

The data suggests that the examples were stable for a period of 1 month at accelerated conditions.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

What is claimed is:

1. A pharmaceutical formulation comprising an aqueous carrier liquid having dissolved therein (a) a glucocorticoid of formula (I)

wherein R represents a 5 membered heterocyclic aromatic ring containing 1 to 3 heteroatoms selected from O, N and S, or a solvate thereof, as a medicament; and
(b) a solubilising agent for assisting the solubilisation of the medicament in the aqueous carrier liquid.

2. A pharmaceutical formulation according to claim 1 wherein the solubilising agent is a surfactant.

3. A pharmaceutical formulation according to claim 2 wherein the surfactant is selected from the group consisting of a α-[4-(1,1,3,3-tetramethylbutyl)phenyl]-ω-hydroxypoly(oxy-1,2-ethanediyl) polymer and a 4-(1,1,3,3-Tetramethylbutyl) phenol polymer with formaldehyde and oxirane.

4. A pharmaceutical formulation according to claim 3 wherein the surfactant is a 4-(1,1,3,3-Tetramethylbutyl)phenol polymer with formaldehyde and oxirane.

5. A pharmaceutical formulation according to claim 2 which further has dissolved therein a hydroxy containing organic co-solvating agent or phosphatidyl choline.

6. A pharmaceutical formulation according to claim 5 wherein the hydroxy containing organic co-solvating agent is dextrose.

7. A pharmaceutical formulation according to claim 1 wherein the formulation further comprises chloride as an isotonic agent.

8. A pharmaceutical formulation according to claim 1 which comprises another therapeutically active agent.

9. A pharmaceutical formulation according to claim 8 wherein the other therapeutically active agent is an anti-histamine or an anti-allergic.

10. A container containing a pharmaceutical formulation according to claim 1, fitted with a metering valve.

11. A device adapted for intranasal delivery of a pharmaceutical formulation comprising a container according to claim 10.

12. A method of treatment of inflammatory and/or allergic conditions of the nasal passages which comprises administering to the nose a pharmaceutical formulation according to claim 1.

13. The method according to claim 12 wherein the administration is once-per-day.

14. A process for preparing a pharmaceutical formulation which comprises:
(a) providing:
(i) a glucocorticoid of formula (I)

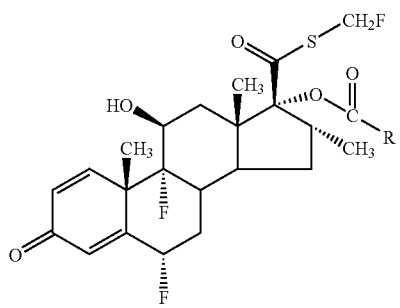

wherein R represents a 5 membered heterocyclic aromatic ring containing 1 to 3 heteroatoms selected from O, N and S, optionally substituted by one or more methyl or halogen atoms or a solvate thereof, as a medicament;
(ii) water and
(iii) a solubilizing agent for assisting the solubilization of the medicament in the aqueous carrier liquid, wherein said solubilizing agent is a surfactant;
(b) dissolving the glucocorticoid of formula (I) in the undiluted surfactant at a temperature of at least 60° C., to form a mixture of glucocorticoid and surfactant;
(c) heating said water to a temperature of at least 60° C., and combining said heated water to said mixture of glucocorticoid and surfactant to achieve the desired concentration of active ingredient;
(d) optionally modifying the pH of the final solution;
(e) filtering the hot solution comprising of water, surfactant and medicament to remove any residual particulate matter.

* * * * *